United States Patent [19]

Inukai et al.

[11] 4,017,416

[45] Apr. 12, 1977

[54] P-CYANOPHENYL 4-ALKYL-4'-BIPHENYLCARBOXYLATE, METHOD FOR PREPARING SAME AND LIQUID CRYSTAL COMPOSITIONS USING SAME

[75] Inventors: Takashi Inukai; Hideo Sato; Shigeru Sugimori; Tetsuya Ishibe, all of Yokohamashi, Japan

[73] Assignee: Chisso Corporation, Osaka, Japan

[22] Filed: Oct. 3, 1975

[21] Appl. No.: 619,539

[30] Foreign Application Priority Data

Oct. 11, 1974 Japan .................. 49-116928
Apr. 12, 1975 Japan .................. 50-44496

[52] U.S. Cl. .................. 252/299; 260/465 D; 350/160 LC
[51] Int. Cl.² .................. C09K 3/34; G02F 1/13
[58] Field of Search .................. 252/299, 408 LC; 350/160 LC; 260/465 D

[56] References Cited

UNITED STATES PATENTS

| | | | |
|---|---|---|---|
| 3,923,857 | 12/1975 | Doller et al. | 252/299 |
| 3,925,238 | 12/1975 | Gavrilovic | 252/299 |
| 3,947,375 | 3/1976 | Gray et al. | 252/299 |
| 3,952,046 | 4/1976 | Scherrer et al. | 252/299 |

FOREIGN PATENTS OR APPLICATIONS

| | | | |
|---|---|---|---|
| 807,165 | 3/1974 | Belgium | 252/299 |
| 814,291 | 8/1974 | Belgium | 252/299 |
| 2,502,904 | 7/1975 | Germany | 252/299 |
| 2,415,929 | 10/1974 | Germany | 252/299 |
| 4,934,488 | 3/1974 | Japan | 252/299 |

OTHER PUBLICATIONS

Morrison; R. T. & Boyd; R. N., *Organic Chemistry*, Allyn & Bacon, Inc., Boston, pp. 440–441, 444–445, 474, 622 (1959).

*Primary Examiner*—Benjamin R. Padgett
*Assistant Examiner*—T. S. Gron
*Attorney, Agent, or Firm*—Fred Philpitt

[57] ABSTRACT

Novel nematic liquid crystal compounds having a broad nematic temperature range and a positive dielectric anisotropy by themselves, that is, p-cyanophenyl 4-alkyl-4'-biphenylcarboxylates wherein the alkyl is a straight chain alkyl group having 4–8 carbon atoms or a branched alkyl group having 4–7 carbon atoms and having methyl group as branched group, and a method for preparing the same are provided. Further, novel nematic liquid crystal compositions having a broader nematic temper range i.e. a sufficiently lower nematic limit and a sufficiently higher upper nematic limit is provided by using said compounds.

2 Claims, 9 Drawing Figures

P-CYANOPHENYL 4-ALKYL-4'-BIPHENYLCARBOXYLATE, METHOD FOR PREPARING SAME AND LIQUID CRYSTAL COMPOSITIONS USING SAME

DESCRIPTION OF THE INVENTION

The present invention relates to novel organic compounds, method for preparing the same and liquid crystal compositions using the same. More particularly, it relates to novel organic compounds which exhibit the state of a nematic liquid crystal having a positive dielectric anisotropy at temperatures of melting point or higher; method for preparing the same; and liquid crystal compositions using the same. Nematic liquid crystals having a positive dielectric anisotropy are used for display apparatuses utilizing an electric field effect brought by impressing a voltage upon a liquid crystal cell having a twisted orientation.

Organic compounds to be used for liquid crystal display apparatuses must be in a nematic state. Accordingly, in order that liquid crystal display apparatuses can be used at temperatures of natural environment, without necessity of being equipped with any particular thermostat apparatus, it is practically required that the nematic temperature range of liquid crystal substance is broad. However, there exists no sole compound wich satisfies such a requirement. Accordingly, compositions consisting of a few kinds of compounds are employed for practical use. Further, for each of the compounds which constitute a liquid crystal composition having a broad nematic temperature range, it is required to have an appropriate temperature region and a nematic temperature range as broad as possible.

Generally, as for the nematic temperature range of a sole compound, even a comparatively broad one is an extent of 50° C. A range of 100° C may be regarded as exceptional. Examples of compounds having such an exceptionally broad temperature range are the following compounds or similar thereto:

These compounds have a negative dielectric anisotropy and cannot be used for the above-mentioned electric field type display apparatuses. As for compounds having a positive dielectric anisotropy as well as a nematic temperature range comparable to those of the above-mentioned compounds, only 4-n-pentyl-4''-cyanoterphenyl (130°–239°) and 4-n-heptyl-4''-cyanoterphenyl (134°–222°) have recently been reported.

The present inventors have searched for compounds having a broad nematic temperature range usable for the above-mentioned object and also having a positive dielectric anisotropy, and as a result, found a group of compounds expressed by by the following formula (I) which are entirely different from the above-mentioned terphenyls:

These compounds are novel ones and prepared by deriving 4-n-alkyl-4'-biphenylcarboxylic acids (expressed by formula II mentioned below) (which are also novel compounds but are, to be regret, not a nematic liquid crystal and exhibit a smectic liquid crystal state) to 4-cyanophenol esters thereof according to a known reaction-procedure. Said 4-n-alkyl-4'-biphenylcarboxylic acids are prepared by acidic or alkaline hydrolysis of 4-n-alkyl-4'-cyanobiphenyls (expressed by formula III mentioned below) or according to our process disclosed in Japanese patent application No. 44496/1975, i.e. by oxydizing 4-alkyl-4'-acetylbiphenyl.

As apparent from the above-mentioned, an object of the present invention is to provide a novel nematic liquid crystal compound which is a simple compound and has a broad temperature range and a positive dielectric anisotropy, and a method for preparing the same.

A further object of the present invention is to provide a novel raw material to be used for nematic liquid crystal compositions.

A still further object of the present invention is to provide a novel liquid crystal compound.

Other objects of the present invention will be apparent from the description mentioned below.

Namely, the present invention resides in:

(1) p-cyanophenyl 4-alkyl-4'-biphenylcarboxylates wherein said alkyl is a straight chain alkyl group having 4–8 carbon atoms or a branched alkyl group having 5–7 carbon atoms and having methyl group as branched group;

(2) A method for preparing p-cyanophenyl 4-alkyl-4'-biphenylcarboxylates wherein said alkyl is a stright chain alkyl group having 4-8 carbon atoms or a branched chain alkyl group having 5-7 carbon atoms and having methyl group as branched group, which is characterized by condensing a 4-alkyl-4'-biphenylcarboxylic acid (wherein said alkyl has the same meaning as defined above) with p-cyanophenol;

(3) A method for preparing p-cyanophenyl 4-alkyl-4'-biphenylcarboxylates according to the above (2) wherein said 4-alkyl-4'-biphenylcarboxylic acid is obtained by hydrolyzing 4-alkyl-4'-cyanobiphenyls wherein said alkyl has the same meaning as defined in (2), with an acid or an alkali;

(4) A method for preparing p-cyanophenyl 4-alkyl-4'-biphenylcarboxylates according to the above (2) wherein said 4-alkyl-4'-biphenylcarboxylic acid is obtained by oxidizing 4-alkyl-4'-acetylbiphenyls wherein said alkyl has the same meaning as defined above;

(5) A liquid crystal composition wherein one or more kinds of p-cyanophenyl 4-alkyl-4'-biphenylcarboxylates defined in the paragraph (1) are used; and

(6) A liquid crystal composition comprising the following 4 groups of (A)–(D):

(A) two or three kinds of compounds selected from the group consisting of 4-alkylbenzoic acid-4'-cyanophenyl esters expressed by the general formula

(IV)

(wherein R is a straight chain alkyl group having 4-8 carbon atoms or a straight chain alkoxy group having 5-8 carbon atoms), said two kinds or at least two of said three kinds of compounds each having as R a straight chain alkyl group,

(B)

alone or a mixture thereof with selected from 4-alkyl-4'-cyanobiphenyls expressed by the general formula (V)

wherein n is 5 or 7, (C) one kind or two kinds or more of compounds selected from the group consisting of 4-alkylbiphenylcarboxylic acid-4'-cyanobiphenyls expressed by the general formula

(VI)

(wherein $C_nH_{2n+1}$ is a straight chain alkyl group having 4-8 carbon atoms or a branched alkyl group having 5-7 carbon atoms and having methyl group as branched group), and (D) one kind or more of compounds selected from the group consisting of 4-n-butylbenzoic acid-4'-alkyl esters (wherein R is n-heptyl group, n-hexyloxy group or n-heptyloxy group) expressed by the general formula (VII)

or 4-anisic acid-4'-n-pentylphenyl ester having a formula of alone or its mixture with said one kind or more of compounds selected from the group consisting of 4-n-butylbenzoic acid-4'-alkyl esters.

Said 4-alkyl-4'-biphenylcarboxylic acids (wherein the alkyl group is a straight chain alkyl group having 4-8 carbon atoms or a branched alkyl group having 5-7 carbon atoms and having methyl group as a branched group) to be used in the present invention, are prepared preferably, as mentioned above, by acidic or alkaline hydrolysis of 4-alkyl-4'-cyanobiphenyls or by oxydation of 4-alkyl-4'-acetylbiphenyls. As for p-cyanophenol to be used in the present invention, those prepared according to a known method or those obtained by purifying commercial products can be used.

The reaction method is carried out, for example, as follows:

4-n-alkyl-4'-cyanobiphenyl is dissolved in sulfuric acid (concentration: 60-80%) in an amount of about several times — ten times the amount of the former, and the resulting solution is heated with stirring under reflux (temperature: about 140°-180° C). The time required is about 1-4 hours after elevation of temperature, 4-n-alkyl-4'-cyanobiphenyl is hydrolyzed into 4-n-alkyl-4'-biphenylcarboxylic acid. After completion of the reaction, the resulting reaction product is cooled down to room temperature, diluted with water in about the same amount as that of the reaction product, and filtered with a glass filter or the like. The resulting filtered product is recrystallized with a suitable solvent such as glacial acetic acid to give purified product of 4-n-alkyl-4'-biphenylcarboxylic acid, which is a colorless crystal having a melting point of 150° C or higher (depending upon the number of carbon atoms of n-alkyl group) and forms a smectic liquid crystal at the melting point or higher temperatures.

4-n-Alkyl-4'-biphenylcarboxylic acid can be also prepared according to the above method (4) of the present invention (Japanese patent application No. 44496/1975). Namely, as described below in the following formulas (1), alkylbiphenylcarboxylic acid (II) is prepared by starting from biphenyl which is a cheap, commercial raw material. Further, a p-cyanophenyl ester (I) which is a final objective product is prepared from said (II).

(II)         (I) ________ (1)

In the above formulas (1) according to the method of the present invention, the first step process is carried out according to conventional Friedel-Krafts reaction. As catalyst, a so-called Friedel-Krafts catalyst such as anhydrous aluminum chloride is used, and as reaction solvent, nitrobenzene or carbon disulfide or solvents having similar effectiveness thereto can be used. As acylating agent, a corresponding acid chloride or the like is used.

Physical properties and yields of 4-acylbiphenyls formed in the first step reaction according to the above or other processes, are shown in Table 1. All of the compounds described in the table are recrystallizate of a raw product with methanol or isopropanol.

Table 1

Physical Properties and Yields of Acylated Biphenyls

R.CO—〈〉—〈〉

| No. | R in side chain | Melting point (°C)[3] | Yield (%) |
|---|---|---|---|
| ① | C—C—C— | 95.9–96.3 (94) | 94 |
| ② | C—C—C—C— | 79–79.5 (76–78) | 95 |
| ③ | C—C—C—C—C— | 95–96 (96.5) | 95 |
| ④ | C—C—C—C—C—C— | 86–86.5 (86.5–86.5) | 94 |
| ⑤ | C—C—C—C—C—C—C— | 99.4–100.0 | 93 |
| ⑥ | C—C—C—C—<br>            C | 39 (64)[1,2] | 91 |
| ⑦ | C—C—C—C—<br>          C | b.p. 172–5° (1 mmHg)<br>57–58° | 72 |
| ⑧ | C—C—C—C—<br>       C | 70–72° (71–72.5) | 71 |
| ⑨ | C—C—C—<br>       C | 74–75.5 (74.0–76.5) | 65 |

Notes:
[1]L.M.Long, H.R. Henze, J. Amer. Chem. Soc. 63 1939 (1941)
[2]The cause of difference from value of literature is unclear.
[3]Numeral values within the parentheses show those of literatures.

The second step reaction process in the above formulas (1) of the present invention can be carried out simply according to Hung-Minlon modification process of known Wolff-Kishner reaction, but it can be also prepared according to a known catalytic reduction method. Physical properties and yields of 4-alkylbiphenyls formed in the second step reaction are shown in Table 2.

Table 2

Physical Properties and Yields of 4-Alkylbiphenyls

R.CH₂—〈〉—〈〉

| No. | R in side chain | (b.p. °C/mmHg) | Yield (%) |
|---|---|---|---|
| ① | C—C—C— | 160–164/6 | 68 |
| ② | C—C—C—C— | 166–167/6 | 70 |
| ③ | C—C—C—C—C— | 144–147/1 | 79 |
| ④ | C—C—C—C—C—C— | 168–172/3 | 80 |
| ⑤ | C—C—C—C—C—C—C— | 181–182/1.5 | 82 |
| ⑥ | C—C—C—C—<br>        C | 140–145/1 | 76 |
| ⑦ | C—C—C—C—<br>      C | 165–170/2 | 70 |
| ⑧ | C—C—C—C—<br>   C | 160–165/2 | 81 |
| ⑨ | C—C—C—<br>   C | 156–157/6 | 82 |

The third step reaction process in the above formulas (1) of the present invention corresponds to a known acetylation reaction according to Friedel-Krafts reaction, and can be carried out according to similar process, utilizing the apparatus employed in the first step process. The physical properties and yields of the acetylated alkylbiphenyls obtained according to the method of the present invention are shown in Table 3.

Table 3

Physical Properties and Yields of 4′-Acetyl-4-Alkylbiphenyls

R.CH₂—〈〉—〈〉—COCH₃

| No. | R in side chain | m.p. (°C) | Yield (%) |
|---|---|---|---|
| ① | C—C—C— | 87–90 | 85 |
| ② | C—C—C—C— | 81–82 | 84 |
| ③ | C—C—C—C—C— | 81–83 | 84 |
| ④ | C—C—C—C—C—C— | 81–83 | 70 |
| ⑤ | C—C—C—C—C—C—C— | 84.2–84.9 | 87 |
| ⑥ | C—C—C—C—<br>        C | 47.4–48.4 | 58 |
| ⑦ | C—C—C—C—<br>      C | 79.5–82 | 69 |
| ⑧ | C—C—C—C—<br>   C | 74–76 | 69 |
| ⑨ | C—C—C—<br>   C | 94–96 | 80 |

The fourth step reaction process in the above formulas (1) of the present invention corresponds to and oxydation reaction carried out with bromine in the medium of alkali, and generally it belongs to a haloform reaction. In this reaction, the objective product can be obtained with a good yield, by carrying out the reaction at 35°–40°C, using a water-soluble solvent such as p-dioxane and also using 14–20 mols of sodium hydroxide and 3.3–5 mols, preferably 3.5–4.0 mols, of bromine per mol of acetylated product as a starting material. Physical properties and yields of the alkylbiphenylcarboxylic acids obtained according to the method of the present invention are shown in Table 4 (cf. Example 10 mentioned below).

Table 4

Physical Properties and Yields of
4'-Alkyl-4-Biphenylcarboxylic acids

R·CH$_2$—⟨⟩—⟨⟩—COOH

| No. | R in side chain | m.p. (° C) | Yield (%) |
|---|---|---|---|
| ① | C—C—C— | 199 | 74 |
| ② | C—C—C—C— | 177 | 84 |
| ③ | C—C—C—C—C— | 170–171 | 75 |
| ④ | C—C—C—C—C—C— | 163 | 77 |
| ⑤ | C—C—C—C—C—C—C— | 151 | 76.5 |
| ⑥ | C—C—C—C—<br>         │<br>         C | 204.7–206.1 | 68 |
| ⑦ | C—C—C—C—<br>       │<br>       C | 205.2–208.2 | 66 |
| ⑧ | C—C—C—C—<br>     │<br>     C | 185–187 | 76 |
| ⑨ | C—C—C—<br>     │<br>     C | 225.5–227.6 | 72 |

All of these compounds exhibit a smectic state at their melting points or higher temperatures. As for the compounds ①–⑤ shown in Table 4, it has been confirmed by mixing said compounds with the corresponding substances and measuring melting points thereof, as disclosed in Japanese patent application No. 116938/1974 (corresponding to the above-mentioned first embodiment (1) of the present invention), that said compounds are identical to those obtained by hydrolysis of the corresponding 4'-alkyl-4-biphenylcarbonitriles. In addition, the elemental analytical values of the compounds ⑥–⑨ in Table 4 are shown in Table 5.

Table 5

Elemental analytical values of
compounds ⑥–⑨ in Table 4

| No. of compounds of Table 4 | Molecular formula | Calculated value | | Analytical value | |
|---|---|---|---|---|---|
| | | C | H | C | H |
| ⑥ | C$_{19}$H$_{22}$O$_2$ | 80.8 | 7.9 | 80.6 | 8.1 |
| ⑦ | C$_{19}$H$_{22}$O$_2$ | 80.8 | 7.9 | 80.8 | 8.1 |
| ⑧ | C$_{19}$H$_{22}$O$_2$ | 80.8 | 7.9 | 80.6 | 8.0 |
| ⑨ | C$_{18}$H$_{20}$O$_2$ | 80.6 | 7.5 | 80.4 | 7.6 |

To a given amount of the above-mentioned biphenylcarboxylic acid is added a molar equivalent or more, preferably 1.2–2.5 molar equivalent, of thionyl chloride, and the resulting mixture is heated under reflux for a given time to form acid chloride, followed by distilling off an excessive amount of thionyl chloride, and adding a suitable inert solvent such as benzene, toluene, etc. to dissolve and dilute the acid chloride.

On the other hand, p-cyanophenol (preferably a purified product) in an equimolecular amount to that of said acid chloride or in a slightly excessive molar ratio is dissolved into several times amount of a water-soluble basic solvent (such as pyridine) capable of dissolving said p-cyanophenol at room temperature, and the resulting solution is cooled. To this cooled solution is dropwise added the above-mentioned solution of acid chloride in an inert solvent, with stirring. After completion of dropwise adding, a mild heating in a water bath or the like is carried out for about one hour. (If an inert solvent such as benzene is used, the reaction mixture is maintained at a constant temperature due to reflux, and hence the use of such solvent is favorable.) After completion of the reaction, the reaction mixture is cooled with ice and poured on ice. To the mixture thus obtained is further added a suitable amount of an inert solvent, and the resulting mixture is transferred to a separating funnel, followed by separating a water layer, washing with dilute hydrochloric acid, washing with a saturated aqueous solution of sodium chloride containing 2% sodium hydroxide, and distilling off the inert solvent, to give a light yellow solid, which is purified with a suitable solvent for recrystallization (such as ethanol) to give a colorless crystal of p-cyanophenyl ester (referred to as formula (I)) of 4-alkyl-4'-biphenylcarboxylic acid (the above-mentioned formula (II)). This crystal forms a nematic liquid crystal at a melting point of about 100° C or higher temperatures (depending upon the carbon numbers of the 4-alkyl group), and the nematic liquid crystal temperature range is 100° C or higher. If the temperature exceeds the range, an isotropic liquid is formed. However, the ester of said formula (I) wherein R=8 forms a smectic liquid crystal at a melting point of 101° C, and forms an isotropic liquid at 202° C.

The compounds of said formula (I) have a broad temperature range as mentioned above, and can be used for liquid crystal displays of electric field effect type, according to the following illustrative method:

1 g of p-cyanophenyl 4-n-hexyl-biphenyl-4'-carboxylate (R=n-C$_6$H$_{13}$ in said formula (I) is dissolved in 29 g of a 3:2 (by mol) mixture of p-methoxy-benzylidene-p'-n-butylaniline and p-ethoxybenzylidene-p'-n-butylanilin. The resulting mixed liquid crystal has a crystallization temperature of 0° C or lower and forms an isotropic liquid at 61° C. This mixed liquid crystal is sealed in a twisted orientation type liquid crystal cell composed of two plates of transparent electrodes of indium oxide subjected to rubbing treatment with cotton cloth in a given direction, and placed between two polarization plates. The behavior of the mixed liquid crystal was investigated using such a known electric field effect type liquid crystal light valve apparatus as prepared above. As a result, it was confirmed that said (I) of (R=n—C$_6$H$_{13}$) has a positive dielectric anisotroy. This mixed liquid crystal has a threshold voltage of electric field effect type response of 4 volt and also a saturation voltage of about 6 volt, each at room temperature.

A 3:2 (by mol) mixture of p-methoxybenzylidene-p'-n-butylaniline and p-ethoxybenzylidene-p'-n-butyl-aniline containing no said (I) of (R=n-C$_6$H$_{13}$) is a nematic mixture which forms an isotropic liquid at 56° C, but it has a negative dielectric anisotropy and hence does not exhibit any electric field effect type response as mentined above.

Further, as for another application example of said (I) compound, the nematic temperature range of a liquid crystal composition composed substantially of only liquid crystal substances having positive dielectric anisotropy is broadened. For example, a eutectic mixture composed of 4-n-pentyl-4'-cyanobiphenyl, 4-n-heptyl-4'-cyanobiphenyl, 4-n-pentyloxy-4'-cyanobiphenyl, 4-n-heptyloxy-4'-cyanobiphenyl and 4-octyloxy-4'-cyanobiphenyl is obtained by mixing these compounds in a ratio of 45%, 24%, 10%,9% and 12% (as expressed by mol fraction) in the above order, and its nematic temperature range is −8° to 50° C. As for this temperature range, its upper limit temperature is insufficient, and this liquid crystal composition readily forms an isotropic liquid in the natural environment where the liquid crystal display apparatus is placed, for example, in case of direct exposure to sun light, whereby the display apparatus is not actuated. In order to elevate the upper limit of the nematic temperature range, it may be readily thought of to make the proportion of a component having a higher upper limit temperature such as 4-n-oxtyloxy-4'-cyanobiphenyl (the upper limit of nematic temperature: 80° C), larger than the above-mentioned proportion. In this case, however, the resulting mixed liquid crystal does not form any eutectic mixture, and the lower limit of the nematic temperature range is elevated, whereby crystal precipitation is liable to occur in the vicinity of 0° C. Whereas a eutectic mixture liquid crystal having a broader nematic temperature range can be prepared by further adding to the above-mentioned five kinds of compounds, any one kind or more of the compounds (I) of the present invention. For example, the composition of a eutectic mixture obtained by simultaneous use of two compounds of formula (I) wherein R=n—$C_5H_{11}$ and R=n—$C_7H_{15}$, of the present invention, is approximately as follows:

4-n-pentyl-4'cyanobiphenyl (42%),
4-n-heptyl-4'-cyanobiphenyl (22%),
4-n-pentyloxy-4'-cyanobiphenyl (9%),
4-n-heptyloxy-4'-cyanobiphenyl (8%),
4-n-octyloxy-4'-cyanobiphenyl (11%),
(I) (R=n—$C_5H_{11}$) (3%), and
(I) (R=n—$C_7H_{15}$) (5%).

The nematic temperature range of this mixed liquid crystal is −11° to 64° C, and even at lower temperatures than the lower limit temperature, the liquid crystal has a large tendency of supercooling and crystal precipitation does not occur readily. However, if the compounds of (I) are added in larger proportions than the above-mentioned, the upper limit temperature increases, but the compounds of (I) precipitate at lower temperatures, and hence the abovementioned proportions are almost optimal. The reason that the nematic temperature range is broadened by adding small amounts of the compounds of (I), is presuned to consist in that (I), R=n—$C_5H_{11}$ has a nematic temperature range as broad as 110°–231° C, by itself, and (I), R=n—$C_7H_{15}$ also has that as broad as 104°–210° C, by itself.

The method for preparing the compounds of (I) of the present invention will be hereunder illustrated by examples. In the following Examples 1–5, as for 4-n-alkylbiphenylcarboxylic acids, those having n-alkyl of 4–8 carbon atoms are shown, but, utterly similar results can be obtained also in case where those having a branched alkyl group of 5–7 carbon atoms having methyl group as branched group are used.

EXAMPLE 1

Preparation of p-cyanophenyl 4-n-pentylbiphenyl-4'-carboxylate (I, R=n-$C_5H_{11}$)

50 Gram of 4-n-pentyl-4'-cyanobiphenyl and 500 g of 70 weight % sulfuric acid were introduced into 2 l three neck flask, and heated on a mantle heater, with stirring under reflux for 2.5 hours. The resulting reaction mixture was water-cooled and then 500 ml of water was added, followed by separating a solid product with a glass filter, water-washing and recrystallizing with glacial acetic acid to give 45.7 g of 4-n-pentyl-biphenyl-4'-carboxylic acid((II), R=$C_5H_{11}$) which was a colorless crystal having a molecular formula of $C_{18}H_{20}O_2$ (composition: C 80.6%, H 7.5%, O 11.9% as calculated values and C 80.3%, H 7.6%, O 12.1% as observed values) and a melting point of 177° C, and formed a smectic liquid crystal at temperatures exceeding the melting point.

Figure 1:
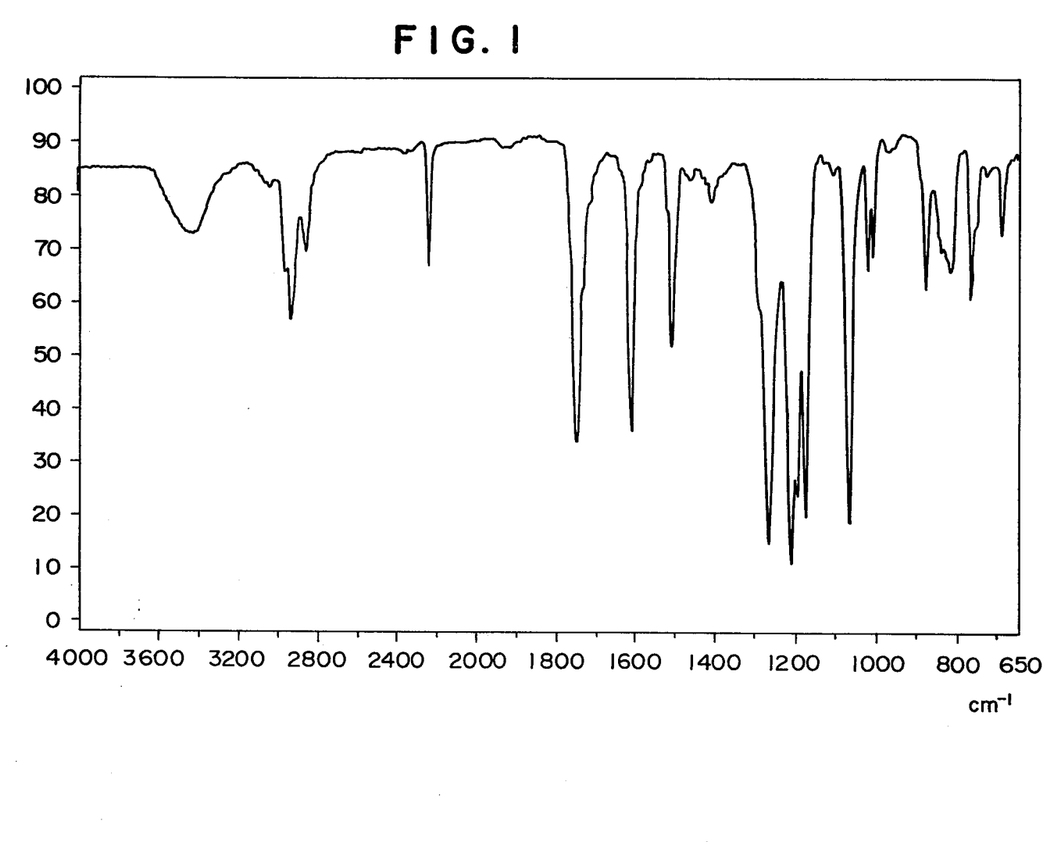
FIGS. 1 – 9 are infrared spectra of specific p-cyanophenyl-4-alkyl-4'-biphenylcarboxylates.

To 45 g of this biphenylcarboxylic acid was added 25 ml (excessive) of thionyl chloride, and the resulting mixture was heated under reflux for one hour to give acid chloride. After distilling off excessive thionyl chloride, 100 ml of benzene was added. To a solution obtained by dissolving 20.5 g of p-cyanophenyl in 80 ml of pyridine and cooled, was dropwise added a benzene solution of the above acid chloride with stirring, followed by heating under reflux on a water bath for one hour, ice-cooling, pouring on ice, further adding 300 ml of benzene, transferring to a separating funnel, removing a water layer, washing with dilute hydrochloric acid, washing with saturated aqueous solution of sodium chloride containing 2% sodium hydroxide, further washing with saturated aqueous solution of sodium chloride and distilling off benzene, to give a light yellow solid, which was recrystallized from ethanol to give 32 g of a colorless crystal ((I), R=$C_5H_{11}$), which had a molecular formula of $C_{25}H_{23}O_2N$ (composition: C 81.3%, H 6.3%, O 8.7%, N 3.8% as calculated values and C 81.4%, H 6.3%, O 8.8%, N 3.6% as observed values) and a melting point of 110° C, and formed a nematic liquid crystal at temperatures exceeding the melting point and an isotropic liquid at 231° C. (Infrared spectrum of (I), R=$C_5H_{11}$ is shown in FIG. 1).

EXAMPLE 2

Preparation of p-cyanophenyl 4-n-hexylbiphenyl-4'-carboxylate ((I), R=n-$C_6H_{13}$)

5 Gram of 4-n-hexyl-4'-cyanobiphenyl, 40 ml of diethylene glycol, 4 ml of water and 2 g of sodium hydroxide were introduced into 200 ml three neck flask and heated with stirring for 25 hours, followed by acidifying with hydrochloric acid, separating by filtration and recrystallizing with glacial acetic acid to give 4.1 g of 4-n-hexyl-biphenyl-4'-carboxylic acid (II), which was a colorless crystal having a molecular formula of $C_{19}H_{22}O_2$ (composition: C 80.8%, H 7.9%, O 11.3% as calculated values and C 80.4%, H 8.1%, O 11.5% as observed values) and a melting point of 170° –171° C and formed a smectic liquid crystal at temperatures exceeding the melting point.

Figure 2:
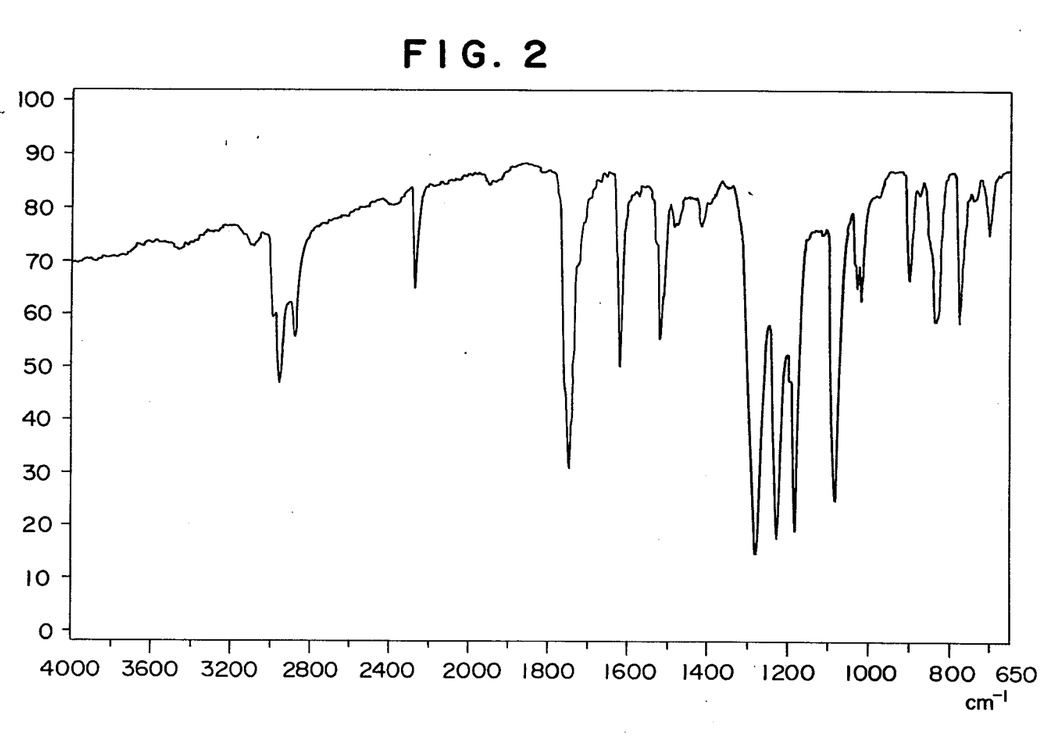

To 3.5 g of this phenylcarboxylic acid was added 5 ml (excessive) of thionyl chloride, and the resulting mixture was heated under reflux for one hour to form acid chloride, followed by distilling off an excessive amount of thionyl chloride, adding 30 ml of benzene, further adding a solution of 1.5 g of p-cyanophenol dissolved in 5 ml of pyridine, heating under reflux for one hour, water-cooling, adding a cold water, transferring to a separating funnel, washing with acid and alkali as in Example 1 and distilling off benzene, to give a light yellow solid, which was recrystallized from ethanol to give 1.5 g of a colorless crystal ((I), R=$C_6H_{13}$), which had a molecular formula of $C_{26}H_{25}O_2N$ (composition: C 81.4%, H 6.6%, O 8.3%, N 3.7% as calculated values and C 81.2%, H 6.8%, O 8.5%, N 3.6% as observed values) and a melting point of 102° C, and formed a nematic liquid crystal at temperatures exceeding the melting point, and an isotropic liquid at 214°. (Infrared spectrum of (I), R=$C_6H_{13}$ is shown in FIG. 2).

EXAMPLE 3

Preparation of p-cyanophenyl 4-n-heptylbiphenyl-4'-carboxylate ((I), R=n-$C_7H_{15}$)

50 Gram of 4-n-heptyl-4'-cyanobiphenyl and 500 g of 70 weight % sulfuric acid were introduced into a 2 l three neck flask and heated on a mantle heater with stirring under reflux for 2.5 hours, followed by water-cooling adding 500 ml of water, separating the resulting solid by filtration with a glass filter, water-washing and recrystallizing with glacial acetic acid, to give 47.3 g of 4-n-heptyl-biphenyl-4'-carboxylic acid ((II), R=$C_7H_{15}$), which was a colorless crystal having a molecular formula of $C_{20}H_{24}O_2$ (composition: C 81.0%, H 8.2%, O 10.8% as calculated values and C 81.2%, H 8.3%, O 10.5% as observed values) and a melting point of 163° C and formed a smectic liquid crystal at temperatures exceeding the melting point.

Figure 3:
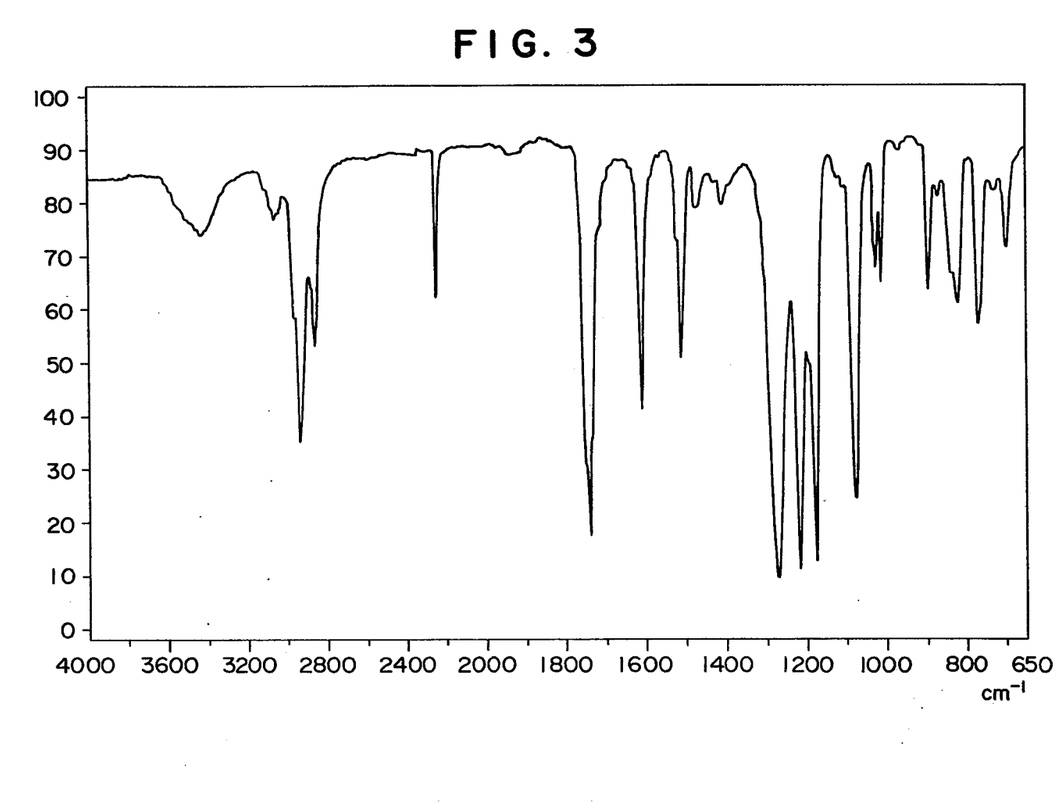

To 47 g of this biphenylcarboxylic acid was added 25 ml (excessive) of thionyl chloride and the resulting mixture was heated under reflux for one hour to form acid chloride, followed by distilling off an excessive amount of thionyl chloride, and adding 400 ml of benzene. To a solution obtained by dissolving 20 g of p-cyanophenol in 80 ml of pyridine and cooled, was dropwise added the above-mentioned benzene solution of acid chloride with stirring, followed by heating on a water bath under reflux for one hour, water-cooling, pouring on ice, transferring to a separating funnel, removing a water layer, washing with dilute hydrochloric acid, washing with a saturated aqueous solution of sodium chloride containing 2% sodium hydroxide, further washing with a saturated aqueous solution of sodium chloride and distilling off benzene, to give a light yellow solid, which was recrystallized from ethanol to give 49.5 g of a colorless crystal ((I), R=$C_7H_{15}$) having a molecular formula of $C_{27}H_{27}O_2N$ (composition: C 81.6%, H 6.8%, O 8.1%, N 3.5% as calculated values and C 81.9%, H 6.8%, O 7.9%, N 3.6% as observed values) and a melting point of 104° C, which formed a nematic liquid crystal at temperatures exceeding the melting temperature and an isotropic liquid crystal at 210° C. (Infrared spectrum of (I), R=$C_7H_{15}$ is shown in FIG. 3.)

EXAMPLE 4

Preparation of p-cyanophenyl 4-n-butylbiphenyl-4'-carboxylate ((I), R=n-$C_4H_9$)

4-n-Butyl-4'-cyanobiphenyl was used as raw material and treatment was carried out in the same manner as in Example 1 to give 4-n-butyl-biphenyl-4'-carboxylic acid ((II), R=$C_4H_9$), which has a colorless crystal having a molecular formula of $C_{17}H_{18}O_2$ (composition: C 80.3%, H 7.1%, O 12.6% as calculated values and C 81.0%, H 6.0%, O - as observed values) and a melting point of 199° C, and formed a smectic liquid crystal at temperatures exceeding the melting point.

Figure 4:
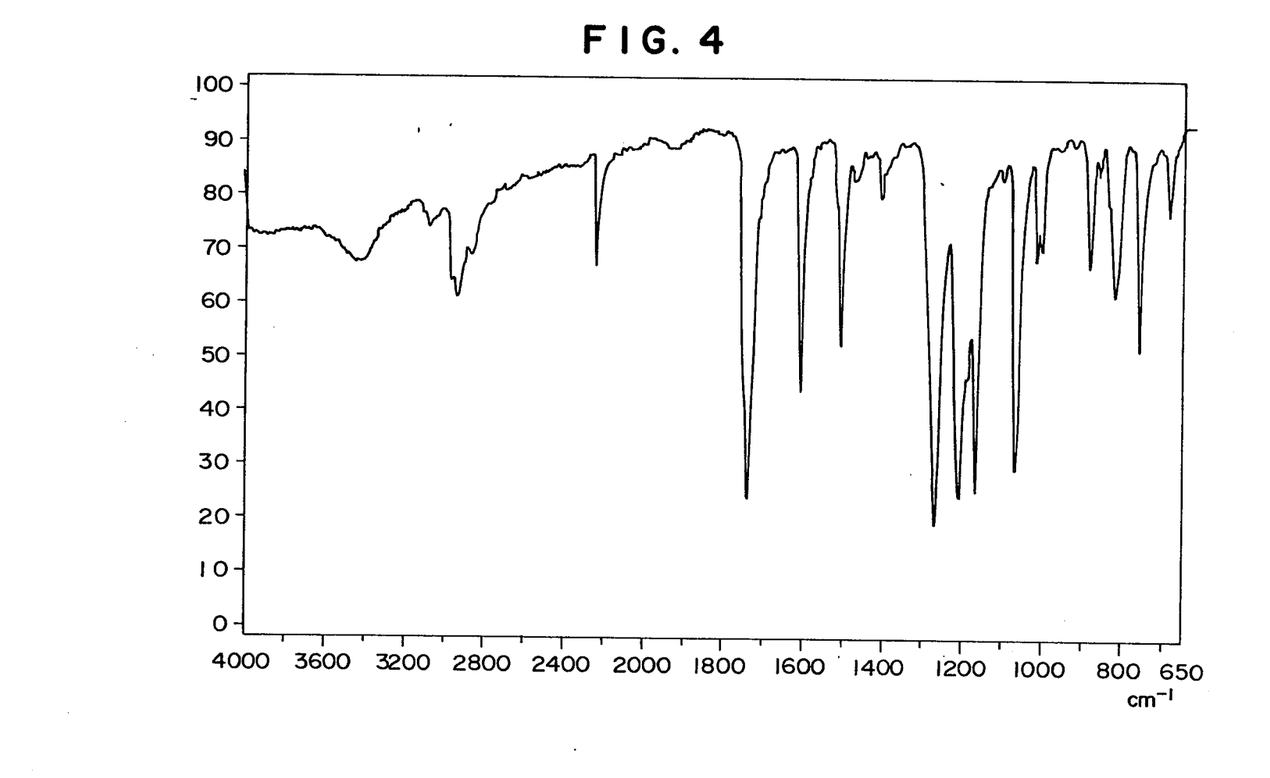

This biphenylcarboxylic acid was reacted with p-cyanophenol in the same manner as in Example 1 and the resulting reaction product was purified to give a colorless crystal ((I), R=$C_4H_9$) having a molecular formula of $C_{24}H_{21}O_2N$ (composition: C 81.1%, H 6.0%, N 3.9%, O 9.0% as calculated values and C 81.0%, H 6.0%, N 3.8%, O - as observed values) and a melting point of 125.2° C, which formed a nematic liquid crystal at temperatures exceeding the melting point and an isotropic liquid at 234° C. (Infrared spectrum of (I) of R=$C_4H_9$) is shown in FIG. 4).

EXAMPLE 5

Preparation of p-cyanophenyl 4-n-octyl-4'-carboxylate (I, R=n-$C_8H_{17}$)

4-n-octyl-4'-cyanobiphenyl was used as raw material, and treatment was carried out in the same manner as in Example 1 to give 4-n-octyl-biphenyl-4'-carboxylic acid (II, R=$C_8H_{17}$), which was a colorless crystal having a molecular formula of $C_{21}H_{26}O_2$ (composition: C 81.3%, H 8.4%; O 10.3% as calculated values, and C 81.1%, H 8.5%, O - as observed values) and a melting point of 151° C and formed a smectic liquid crystal at temperatures exceeding the melting point.

Figure 5:
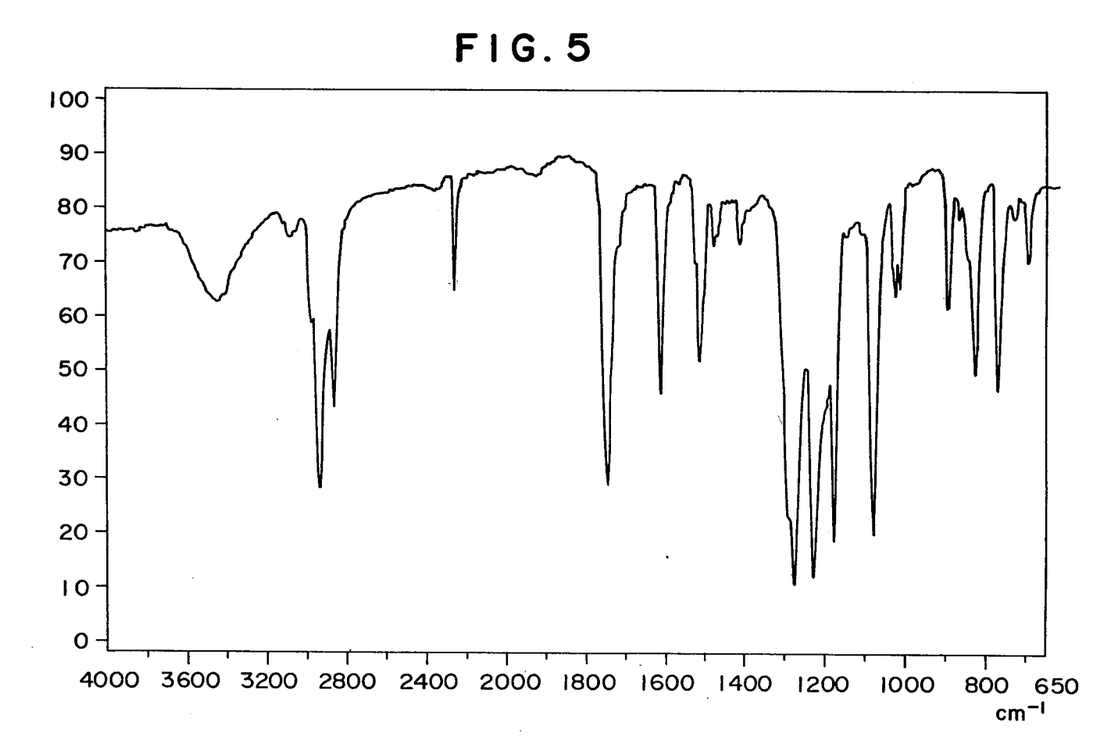
Figure 6:
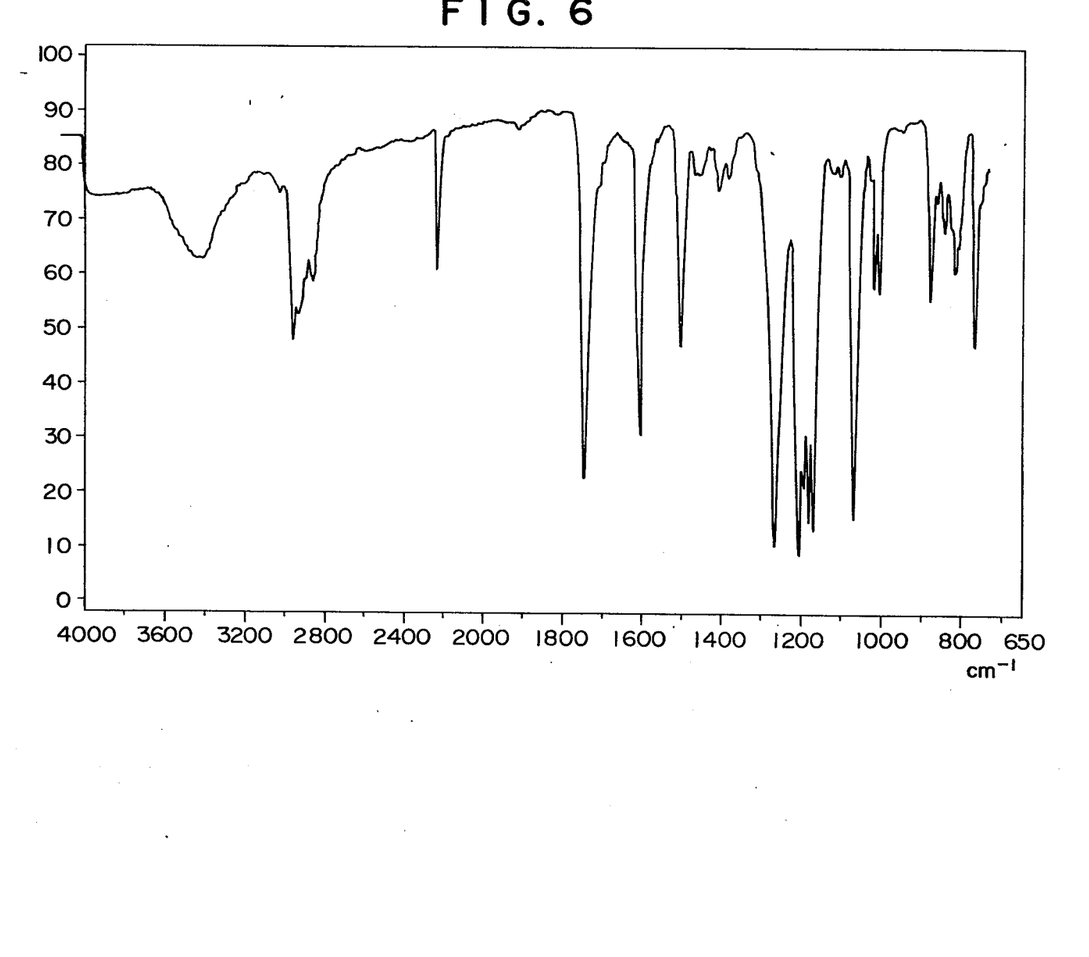
Figure 7:
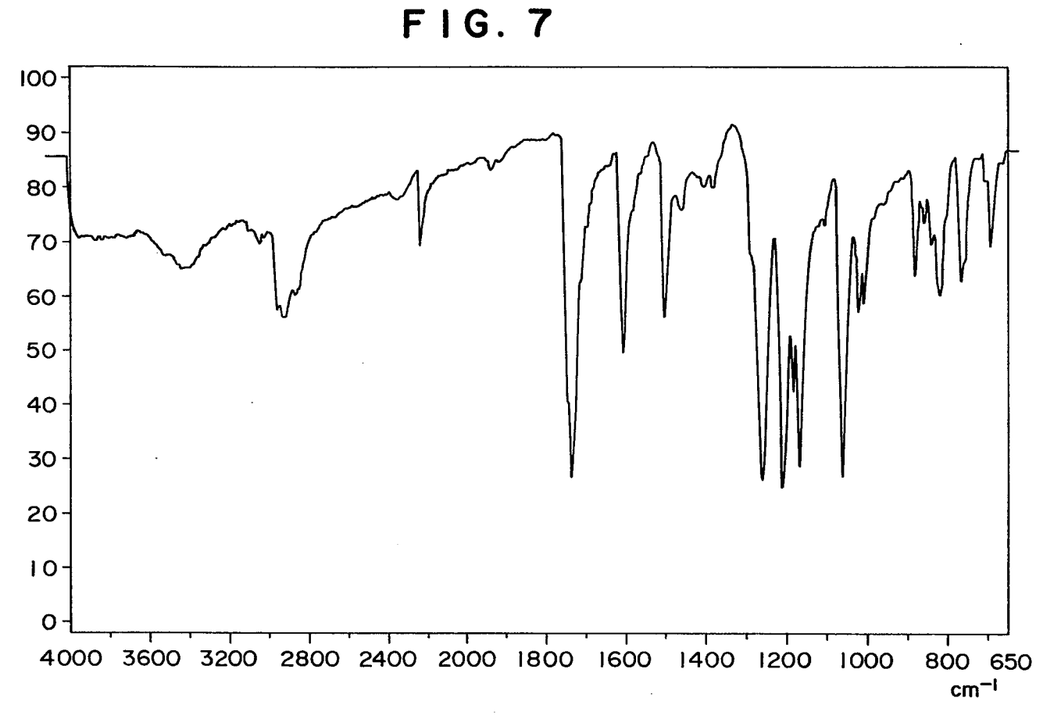
Figure 8:
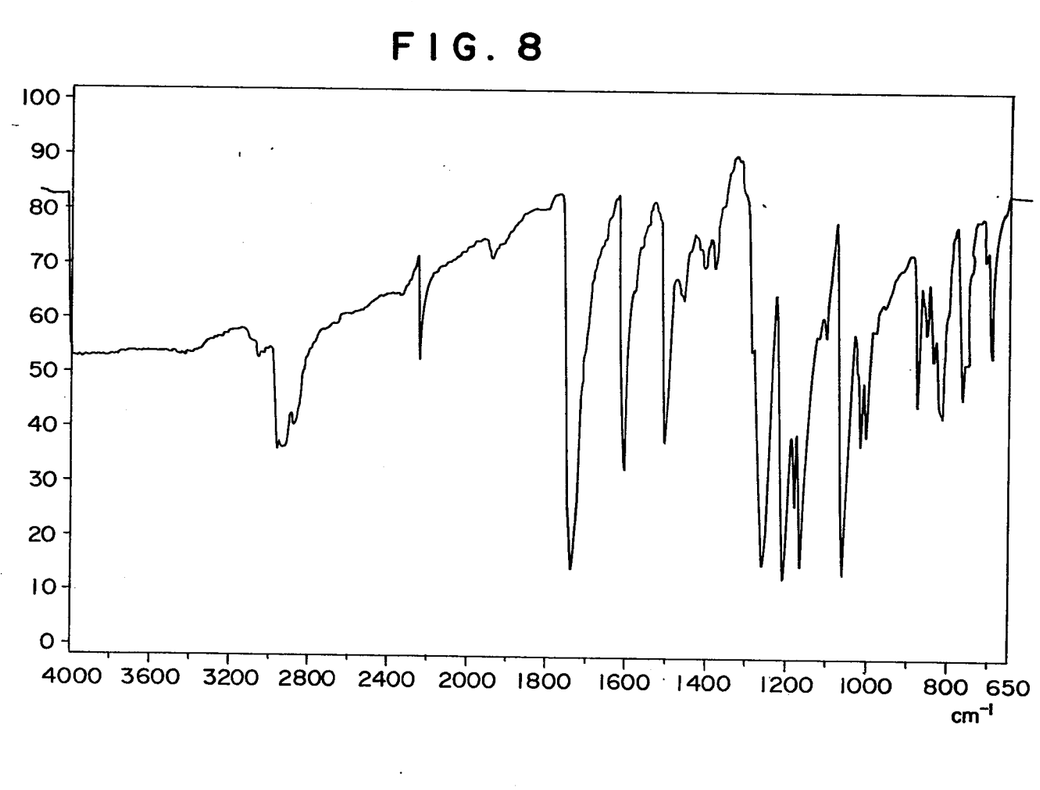
Figure 9:
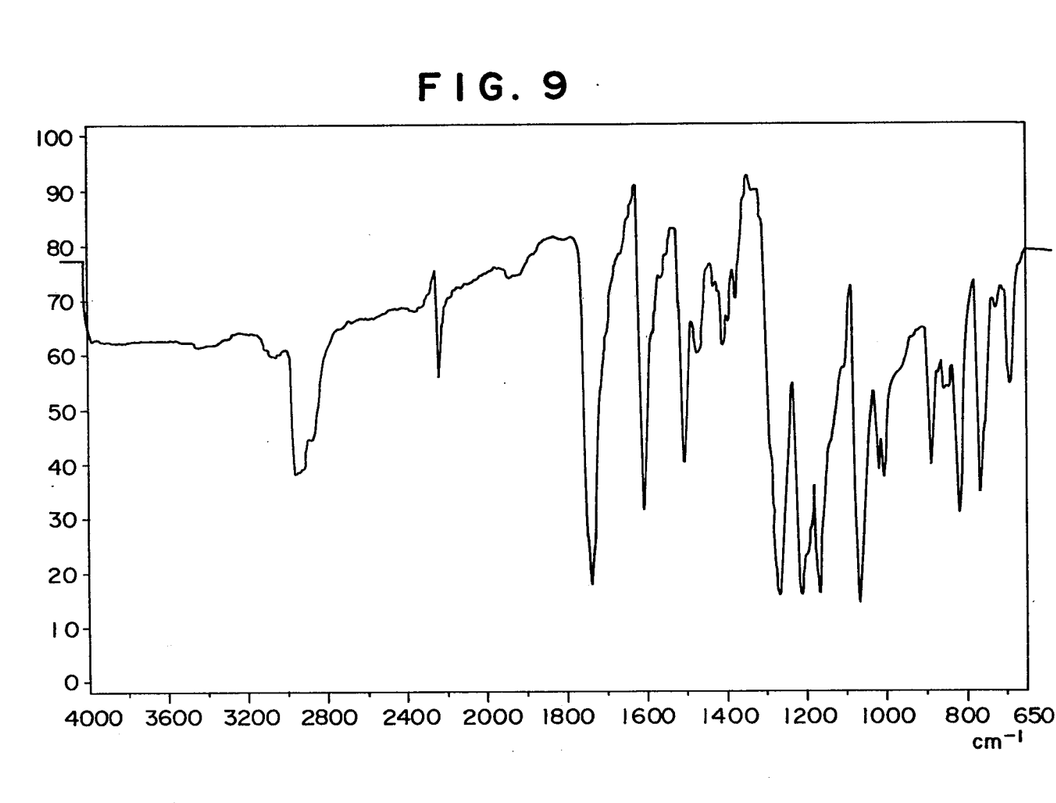

This biphenylcarboxylic acid was reacted with p-cyanophenol in the same manner as in Example 1 and the resulting reaction product was purified to give a colorless crystal (I, R=$C_8H_{17}$), having a molecular formula of $C_{28}H_{29}O_2N$ (composition: C 81.7%, H 7.1%, N 3.4%, O 7.8% as calculated values and C 81.5%, H 7.1%, N 3.4%, O - as observed values) and a melting point of 101° C, which formed a smectic liquid crystal at temperatures exceeding the melting point and an isotropic liquid at 202° C. (Infrared spectrum of (I, R=$C_8H_{17}$) is shown in FIG. 5.)

EXAMPLES 6–9

Using 4'-alkyl-4-biphenylcarboxylic acids ⑥–⑨ described in the above-mentioned Table 4, processes were carried out as in Example 1 to give the corresponding p-cyanophenyl esters (compounds ⑩ – ⑬ in Table 6.

Table 6 p-cyanophenyl esters from compounds 6–9 of Table 4

| No. | R in side chain | Nematic temperature range | Elemental analysis Calculated values C H | Analytical values C H | Yield (%) |
|---|---|---|---|---|---|

Table 6-continued p-cyanophenyl esters from compounds ⑥-⑨ of Table 4

R.CH₂―⟨⟩―⟨⟩―COO―⟨⟩―CN (III)

| No. | R in side chain | Nematic temperature range | Elemental analysis Calculated values | | Analytical values | | Yield (%) |
|---|---|---|---|---|---|---|---|
| ⑩ | C—C—C—C—<br>    \|<br>    C | 125.5–187.5 | 81.4 | 6.6 | 81.3 | 6.4 | 74 |
| ⑪ | C—C—C—C—<br>      \|<br>      C | 105.5–193.9 | 81.4 | 6.6 | 81.3 | 6.6 | 80 |
| ⑫ | C—C—C—C—<br>    \|<br>    C | 102.3–204.4 | 81.4 | 6.6 | 81.2 | 6.6 | 78.5 |
| ⑬ | C—C—C—<br>    \|<br>    C | 145.1–208.4 | 81.4 | 6.3 | 81.2 | 6.1 | 82 |

Infrared spectra of compounds ⑩-⑬ of Table 6 are shown in FIGS. 6–9.

Carboxylic acid (formula II) is obtained by using the 1st to 4th process of above equation (1). Example 10 shows this.

EXAMPLE 10

Preparation of 4′-n-pentyl-4-biphenylcarboxylic acid (compound ② of Table 4)

First step

560 Gram of granular anhydrous aluminum chloride and 1 $l$ of nitrobenzene were introduced into a 5 $l$ three neck flask, and stirred under water-cooling to give a solution. A solution of 600 g of diphenyl and 482.5 g of n-valeric acid chloride dissolved in 1 l of nitrobenzene (prepared in advance) was dropwise added into said three neck flask over 2 hours. After the addition, the resulting mixture was stirred for one hour as it was. Thereafter it was stirred at 40°–45° C for 2 hours, cooled to room temperature, poured cautiously into a mixed solution of 1.3 $l$ of conc. hydrochloric acid and 1.5 $l$ of water for decomposing the catalyst, and cooled to 20° C. Precipitated crystal was separated by filtration. Nitrobenzene was distilled off from nitrobenzene layer by distillation under a reduced pressure to give an additional crystal. Both the crystals were recrystallized from ethanol to give 881 g of crystal of 4-n-pentanoyl-biphenyl (m.p. 79°–79.5° C) (yield: 95% based on biphenyl).

Second Step

Thousand gram of 4-n-pentanoylbiphenyl, 2 $l$ of diethylene glycol and 564 g of potassium hydroxide were introduced into a 5 $l$ three neck flask and warmed with stirring to give a uniform solution at about 80° C, which was then cooled to about 50° C, followed by adding 738 ml of hydrazine hydrate, heating with stirring, distilling off low boiling fractions (mainly water) until the temperature of the reaction mixture reached 185° C, heating under reflux at 185°–190° C for 4 hours, cooling to room temperature, adding 1.5 $l$ of water and 400 ml of hexane, stirring, washing hexane layer with aqueous solution of sodium chloride, and distilling, to give 659 g of 4-n-pentylbiphenyl (b.p. 166°–167°/6 mmHg) (Yield 70%).

Third step

392 Gram of granular anhydrous aluminum chloride and 700 ml of nitrobenzene were introduced into 5 $l$ three neck flask, and dissolved with stirring. A solution of 600 g of 4-n-pentylbiphenyl and 220 g of acetyl chloride dissolved in 500 ml of nitrobenzene (prepared in advance) was dropwise added to said three neck flask over 1 hour, followed by stirring for one hour, further stirring at 40°–45° C for 2 hours, cooling to room temperature, pouring cautiously into a mixed liquid of 250 ml of conc. hydrochloric acid and 1.25 $l$ of water, distilling off nitrobenzene from nitrobenzene layer by distillation under a reduced pressure, separating the resulting solid by filtration, and recrystallizing it from ethanol, to give 597 g of 4′-n-pentyl-4-acetyl-biphenyl (m.p. 81°–82°) (Yield 84%).

Fourth step

883 Gram of 4′-n-pentyl-4-acetylbiphenyl was introduced into a 30 $l$ stainless steel reactor (provided with a stirrer, a reflux condenser and a funnel for dropwise adding), added 3.75 $l$ of p-dioxane and dissolved with stirring. On the other hand, 1.8 kg of bromine was dropwise added to and dissolved in a solution of 2 kg of sodium hydroxide dissolved in 7.5 $l$ of water, cooled to 10°–15° C. The resulting hypobromous acid solution was maintained at about 10° C. This solution was dropwise added to the above-mentioned p-dioxane solution over 50 minutes, followed by stirring at 35°–40° C for 3 hours, allowing to stand over one night, adding 250 g of sodium bisulfite, stirring, neutralizing with 2.8 $l$ of conc. hydrochloric acid, separating the resulting solid by filtration, water-washing, drying and recrystallizing from 6 $l$ of acetic acid, to give 747 g of 4′-n-pentyl-4-biphenylcarboxylic acid of m.p. 177° C (smectic liquid crystal being formed) (Yield 84%).

This product was subjected to mixed examination with 4′-n-pentyl-4-biphenylcarboxylic acid obtained by Example 1 and exhibited no m.p. depression. Further both enfrared absorption spectra were also same. Thus it was confirmed that both were identical substances.

EXAMPLE 11

Preparation of compounds ③-⑨ in Table 4

In entirely the same manner as in Example 10, reactions of the first step to the fourth step of the above-mentioned formula (1) were carried out using diphenyl and the corresponding acid chloride as starting materials, to give compounds ③-⑨ of the above-mentioned Table 4 as ultimate products.

Next, Examples and Referential examples relative to the liquid crystal compositions of the present invention will be hereunder described.

As mentioned above, the liquid crystal compositions of the present invention are those using one kind or more of p-cyanophenyl esters of 4-alkyl-4'-biphenyl-carboxylic acids (wherein the alkyl is a straight chain alkyl group having 4–8 carbon atoms or a branched alkyl group having 5–7 carbon atoms and having methyl group as branched group) (these esters being hereinafter referred to as p-cyanophenyl ester of the present invention).

Among them, the following liquid crystal composition exhibits superior properties:

Liquid crystal compositions consisting of ① p-cyanophenyl ester of the present invention, ② specified p'-cyanophenyl p-alkylbenzoate, ③ specified p-alkyl-p'-cyanobiphenyl and ④ specified p-n-butylbenzoic acid-p'-n-alkyl ester or p-anisic acid-p'-n-pentylphenyl ester.

With regard to the liquid crystal compositions of the present invention or the embodiment (6) of the present invention, the using manners of compounds within groups (A), (B), (C) and (D) will be hereunder explained.

As for compounds (IV) of groups (A), two or three kinds are selected, and at least two kinds have each an alkyl group as R in the formula (IV). If two kinds or more of compounds each having an alkoxy group as R in the formula (IV) are selected, the lower limits of the nematic temperature ranges of liquid crystal compositions are not sufficiently reduced, and the working characteristics at lower temperatures are inferior. Further, even if 4 kinds or more of the compounds of group (A) are employed, the properties of liquid crystal compositions are not improved. The amounts of compounds of group A to be used are 35–50%, preferably 40–47% by mol, based upon the total amount of the compositions.

The amounts of compounds of group B to be used are 20–30% by mol based upon the total amount of the compositions.

Among compounds of formula (V), that of ($n=5$) has a nematic temperature range of 22.5°–35° C and that of ($n=7$) has a nematic temperature range of 28°–42° C. Accordingly, if they are used in an amount exceeding 30%, the upper limits of the nematic temperature ranges of liquid crystal compositions are reduced to an undesirable extent for the object of the present invention, for example, below 50° C. (V) ($n=7$) is preferably used as a 2:1 (by mol) mixture with (V) ($n=5$). The presence of compounds of group (B) contributes notably to the increase in the response speed of electro-optical effect of liquid crystal compositions.

Compounds of group (C) are specified one or ones among novel compounds of the embodiment (1) of the present invention, and one kind may be usually employed in an amount of 8–13% by mol based upon the compositions.

If two kinds or more are employed in suitable amounts, there are obtained effectiveness in elevating the upper limits of the nematic temperature ranges of liquid crystal compositions but not in elevating the lower limits of the ranges. However, if they are used in an amount exceeding 13% by mol, there occurs a tendency of reducing the response velocity of the compositions, and hence such is undesirable for usual object of display.

Finally as for the use of compounds of group (D), it has an effectiveness of reducing the lower limits of the nematic temperature ranges of liquid crystal compositions and thereby broadening the temperature ranges. Preferable added amounts are 15–30% by mol.

The liquid crystal compositions of the embodiment (6) of the present invention shown in Examples 12–14 mentioned below can maintain a nematic state over about −10° C to 60° C, and even when they are allowed to stand at −20° C for several weeks, no crystal precipitation occurs. Further the response velocities are sufficiently large.

EXAMPLE 12

16.8 Gram of 4-n-butylbenzoic acid-4'-cyanophenyl ester (IV, R=$n$—C$_4$H$_9$), 19.3 g of 4-n-heptylbenzoic acid-4'-cyanophenyl ester (IV, R=$n$—C$_7$H$_{15}$), 13.5 g of 4heptyloxybenzoic acid 4'-cyanophenyl ester (IV, R=C$_7$H$_{15}$O), 10.7 g of 4-n-heptylbiphenylcarboxylic acid-4'-phenyl ester (IV, $n=7$), 28.9 g of 4-n-pentyl-4'-cyanobiphenyl (V, $n=5$), and 34 g of 4-n-butylbenzoic acid-4'-n-heptyloxyphenyl ester (VII, R=C$_7$H$_{15}$O), were mixed on heating under degassing in a Schlenk tube to give a liquid crystal composition. The clear point (nematic-isotropic transition temperature) was 60° C, and only when it was allowed to stand at −20° C for a long time, there was formed a crystal, which, however, melted at −5° C and formed a nematic phase.

When this composition was used for a cell for rotating polarized light having a twisted angle of 90° (so-called Twisted Nematic Type Cell), the response threshold voltage (voltage required for 10% response) was 1.2 V, and the response saturation voltage (90% response) was 1.8 V, and when it was driven at 3 V, the rise time was 80 milliseconds, while the decay time was 150 milliseconds. In the above measurement, the temperature was 25° C and the frequency used was 32 Herz.

EXAMPLE 13

16.8 gram of 4-n-butylbenzoic acid-4'-cyanophenyl ester (IV, R=n—C$_4$H$_9$), 18.5 g of 4-n-hexylbenzoic acid-4'-cyanophenyl ester (IV, R=$n$—C$_6$H$_{13}$), 19.3 g of 4-n-heptylbenzoic acid-4'-cyanophenyl ester (IV, R=$n$—C$_7$H$_{15}$), 28.9 g of 4-n-pentyl-40'-cyanobiphenyl (V, R=n—C$_5$H$_{11}$), 15.3 g of 4-n-pentylbiphenylcarboxylic acid-4'-cyanophenyl ester (VI, $n=5$), and 27.0 g of 4-n-butylbenzoic acid-4'-n-heptyloxyphenyl ester (VII, R=C$_7$H$_{15}$O), were mixed in the same manner as in Example 12 to give a liquid crystal composition. The nematic-isotropic transition temperature was 64° C, and only when the composition was allowed to stand at −20° C for a long time, there was formed a crystal, which, however, melted at −10° C and formed a nematic phase. When this composition was used for the same cell for rotating polarized light as in Example 12, the response threshold voltage (voltage required for 10% response) was 1,2 V, while the response saturation voltage (90% response) was 1.8 V. When it was driven at 3 V, the rise time was 80 milliseconds and the decay time was 130 milliseconds. The measurement temperature and frequency used were both same with those of Example 12.

EXAMPLE 14

12.28 gram of 4-n-butylbenzoic acid-4'-cyanophenyl ester (IV, R=n—C$_4$H$_9$), 14.13 g of 4-n-heptylbenzoic acid-4'-cyanophenyl ester (IV, R=n—$C_7H_{15}$), 9.47 g of 4-n-hexyloxybenzoic acid-4'-cyanophenyl ester (IV, R=n—$C_6H_{13}O$), 18.26 g of 4-n-pentyl-4'-cyanobiphenyl (V, R=n—$C_5H_{11}$), 9.31 g of 4-n-heptylbiphenylcarboxylic acid-4'-cyanophenyl ester (VI, n=7), and

16.55 g of 4-anisic acid 4'-n-pentylphenyl ester (substitute compound for VII), were mixed in the same manner as in Example 12 to give a liquid crystal composition. The nematic-isotropic transition temperature was 67° C, and only when the composition was allowed to stand at −20° C for a long time, there was formed a crystal, which, however, melted at −10° C and formed a nematic phase. When this liquid crystal composition was used for the same cell for rotating polarized light as in Example 12, the response threshold voltage (voltage required for 10% response) was 1.0 V while the response saturation voltage (90% response) was 1.7 V. When it was driven at 3 V, the rise time was 80 milliseconds and the decay time was 130 milliseconds. The measurement temperature and frequency used were both same with those of Example 12.

What is claimed is:

1. A liquid crystal composition comprising the following 4 groups of (A)–(D) in the proportions specified:

A. 35–50% by mol, based upon the total amount of the composition, of two or three compounds selected from the group consisting of 4-alkylbenzoic acid-4'-cyanophenyl esters expressed by the general formula (wherein R is a straight chain alkyl group having 4–8 carbon atoms or a straight chain alkoxy group having 5–8 carbon atoms), said two or at least two of said three compounds each having R as a straight chain alkyl group,

B. 20–30% by mol, based upon the total amount of the composition, of or a mixture thereof with C. 8–13% by mol, based upon the total amount of the composition, of one or two or more of compounds selected from the group consisting of 4-alkylbiphenylcarboxylic acid-4'-cyanobiphenyls expressed by the general formula -(wherein $C_nH_{2n+1}$ is a straight chain alkyl group having 4–8 carbon atoms or a methyl branched alkyl group having 5–7 carbon atoms, and D. 15–30% by mol, based upon the total amount of the composition, of one or more compounds selected from the group consisting of 4-n-butylbenzoic acid-4'-alkyl esters (wherein R is n-heptyl group, n-hexyloxy group or n-heptyloxy group) expressed by the general formula and 4-anisic acid-4'-n-pentylphenyl ester having a formula of alone or in admixture with said one or more compounds selected from the group consisting of the above 4-n-butylbenzoic acid-4'-alkyl esters.

2. A liquid crystal composition according to claim 1 wherein the content of two or three of said 4-alkylbenzoic acid-4'-cyanophenyl esters is 40–47% by mol, based upon the total amount of the composition.

* * * * *